(12) United States Patent  
Stellon et al.

(10) Patent No.: US 6,432,085 B1
(45) Date of Patent: Aug. 13, 2002

(54) SELF-RETAINING SURGICAL ACCESS INSTRUMENT

(75) Inventors: Gene Stellon, Southington; David C. Racenet, Southbury, both of CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/521,438

(22) Filed: Mar. 7, 2000

Related U.S. Application Data
(60) Provisional application No. 60/124,855, filed on Mar. 17, 1999.

(51) Int. Cl.$^7$ ............................................... A61M 5/178
(52) U.S. Cl. ................... 604/164.04; 604/174
(58) Field of Search ............................ 604/27, 103.03, 604/164.07, 164.08, 164.11, 174, 264, 158, 109, 272, 165.01, 166.01, 170.01, 164.04

(56) References Cited

U.S. PATENT DOCUMENTS

| 4,601,710 | A |   | 7/1986  | Moll |
|-----------|---|---|---------|------|
| 5,147,316 | A | * | 9/1992  | Castillenti .................... 604/164 |
| 5,217,441 | A |   | 6/1993  | Shichman |
| 5,478,329 | A |   | 12/1995 | Ternamian |
| 5,601,559 | A | * | 2/1997  | Melker et al. ................ 606/79 |
| 5,697,913 | A |   | 12/1997 | Sierocuk et al. |
| 5,755,697 | A | * | 5/1998  | Jones et al. .................. 604/174 |
| 5,817,062 | A | * | 10/1998 | Flom et al. ................... 604/174 |
| 5,857,999 | A | * | 1/1999  | Quick et al. .................. 604/107 |
| 6,056,778 | A | * | 5/2000  | Grafton et al. ................ 623/20 |

FOREIGN PATENT DOCUMENTS

| WO | 9308729 | 5/1993 |
|----|---------|--------|
| WO | 9714454 | 4/1997 |

* cited by examiner

*Primary Examiner*—Brian L. Casler
*Assistant Examiner*—Kevin C. Sirmons

(57) ABSTRACT

A surgical access device for permitting introduction of instrumentation within tissue, includes an elongate member defining a longitudinal axis and proximal and distal ends, a first peripheral projection disposed on an outer wall of the elongate member and defining a proximal ledge dimensioned to resist movement of the elongate member in a first longitudinal direction corresponding to a withdrawal direction of the elongate member with respect to the tissue, a second peripheral projection disposed on the outer wall of the elongate member proximal of the first peripheral projection and defining a distal ledge dimensioned to resist movement of the elongate member in a second longitudinal direction corresponding to an insertion direction of the elongate member with respect to the tissue whereby the first and second peripheral projections cooperate to retain the elongate member within the tissue.

13 Claims, 4 Drawing Sheets

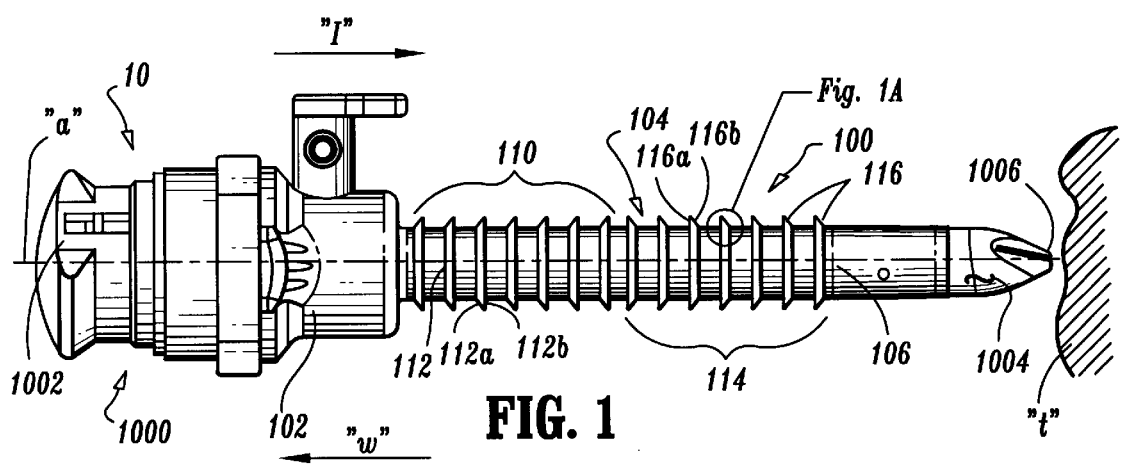
FIG. 1
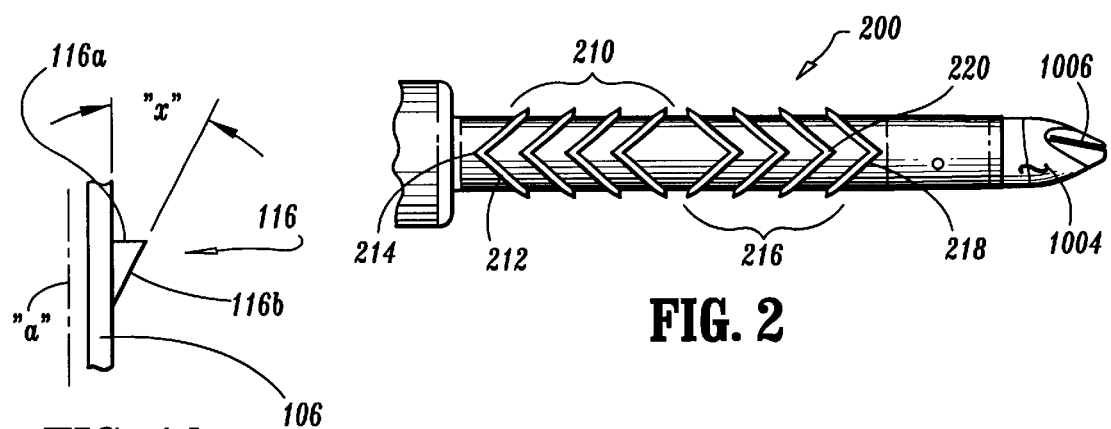
FIG. 1A
FIG. 2
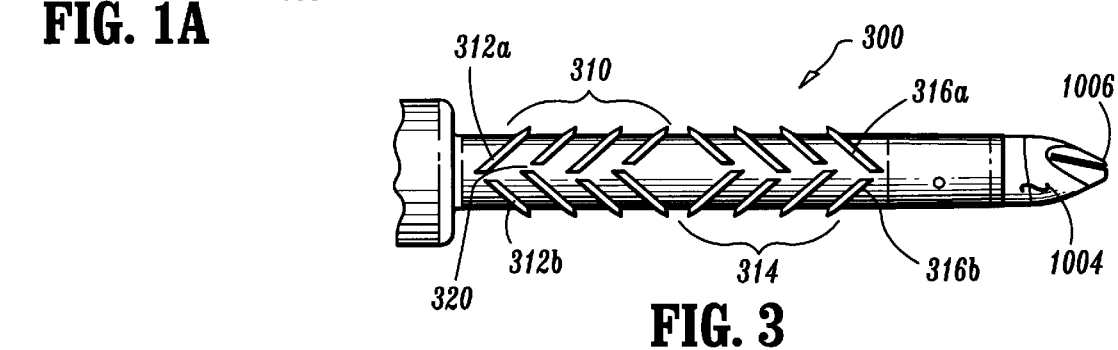
FIG. 3
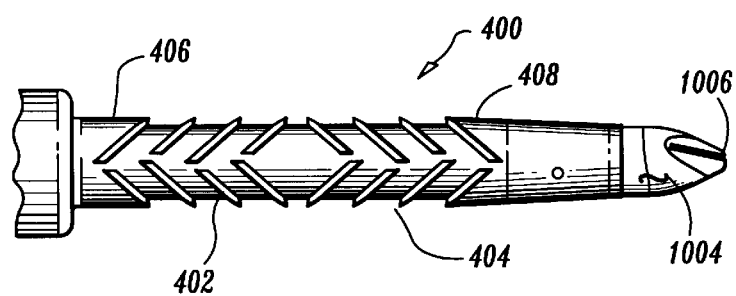
FIG. 4

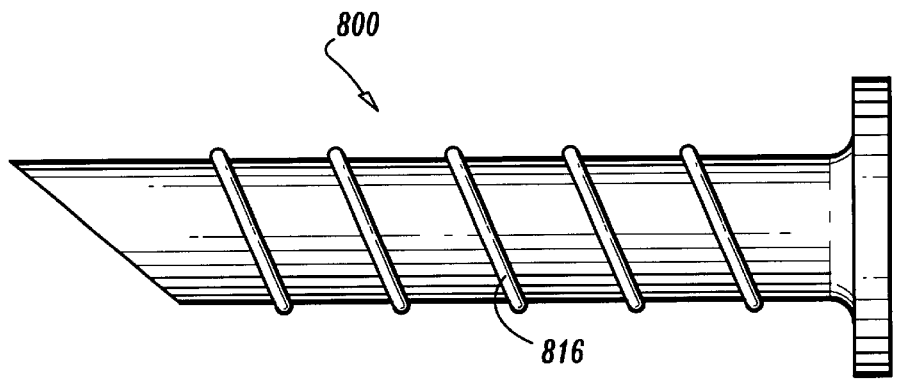
FIG. 8
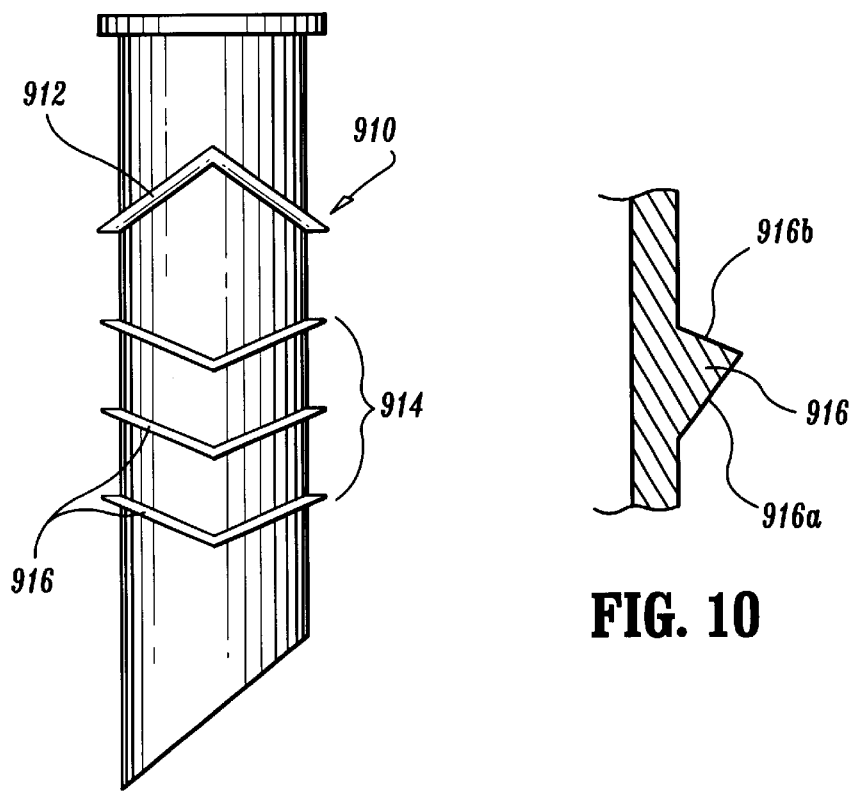 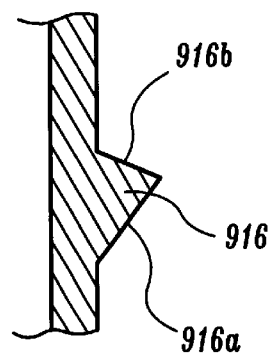
FIG. 9
FIG. 10
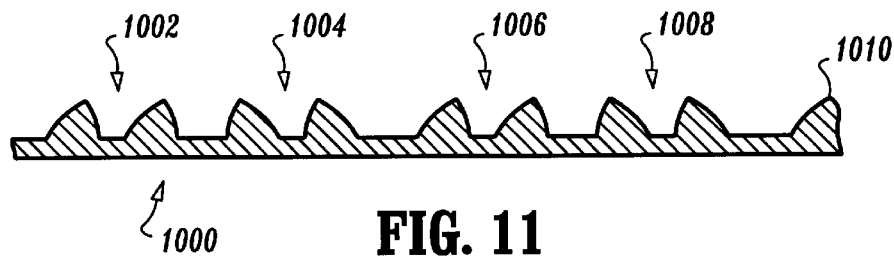
FIG. 11

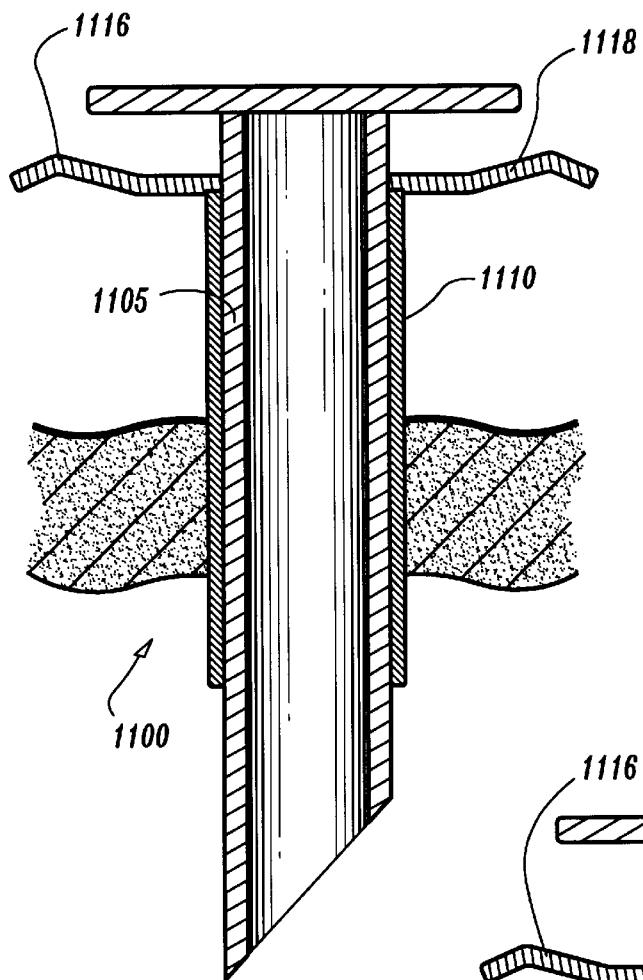
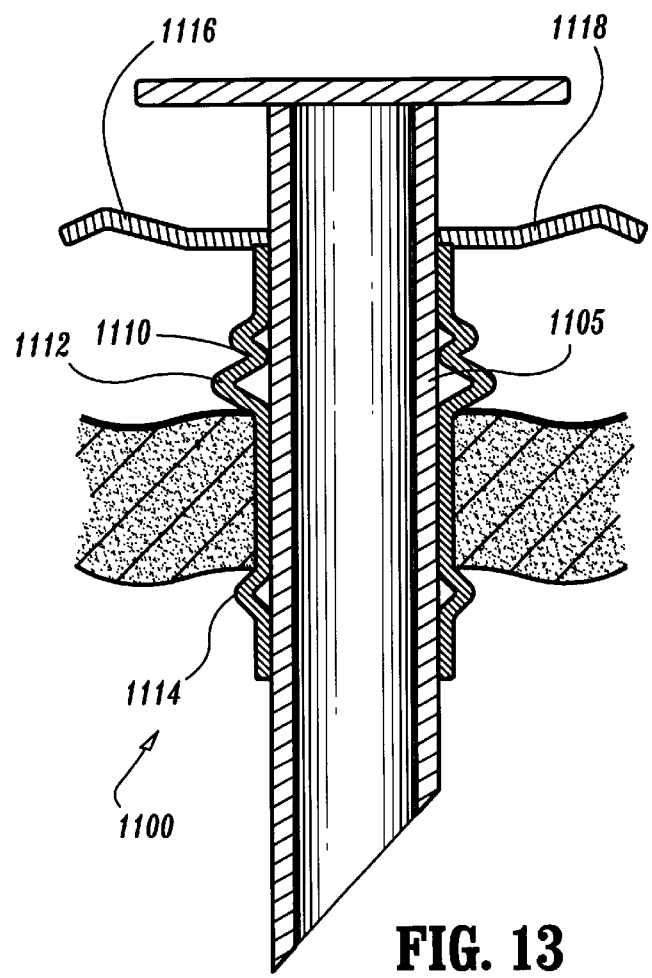

SELF-RETAINING SURGICAL ACCESS INSTRUMENT

This application claims priority from provisional application No. 60/124,855, Mar. 17, 1999.

TECHNICAL FIELD

The present invention generally relates to surgical instruments for performing laparoscopic and endoscopic surgical procedures, and, more particularly, relates to a self-retaining cannula assembly incorporating a novel retention mechanism for securing the cannula within an incision in a patient's body while preventing over insertion of the cannula during application.

BACKGROUND OF THE INVENTION

In laparoscopic and endoscopic surgical procedures, a small incision or puncture is made in the patient's body to provide access for a tube or a cannula device which is inserted into the patient's body to permit for viewing of the surgical site or for the insertion of instruments used in performing the surgical procedure. Typically, a trocar device is used to penetrate the body wall, whereby a sharpened point or tip of the trocar assembly creates the path to the surgical site. A cannula is provided as part of the trocar assembly such that when the pointed piercing mechanism is removed, the cannula remains in place to maintain access to the surgical site. Several incisions may be made to provide numerous access ports to the surgical objective, and once the cannulas are in place, various surgical instruments such as scissors, dissectors, retractors or the like, may be employed by a surgeon to perform the surgery. Typically, a scope device is used to view the area directly, or a miniature camera is used to display the surgical site on a video monitor in the operating room.

In order to maintain the cannula within the incision, it has been known to provide various mechanisms such as external sleeves, expandable members, etc. which engage the tissue surrounding the incision to prevent undesired removal of the cannula. However, such known mechanisms are generally complex in nature. Moreover, these mechanisms often are potentially invasive to the surrounding tissue thereby increasing the likelihood of undesired tissue tear which consequently increases patient trauma and recovery time. Another deficiency in known cannulas of this type concerns the lack of structure to prevent over insertion of the cannula during application within the surgical site.

SUMMARY OF THE INVENTION

Accordingly, the present invention is directed to a cannula including a novel tissue gripping arrangement which supports the cannula in an incision in the patient's body to provide access to the abdominal cavity during, for example, a laparoscopic or endoscopic surgical procedure. In a preferred embodiment, the cannula includes tissue gripping elements which are arranged to facilitate insertion of the cannula within the cavity by, for example, minimizing insertion force required to advance the cannula relative to the operative site while also restricting removal of the cannula by increasing the withdrawal force required to remove the cannula. Furthermore, several of the tissue gripping elements are specifically adapted to engage the tissue upon insertion of the cannula a predetermined distance to thereby minimize the potential of overinsertion of the cannula relative to the operative site thereby avoiding potential consequences to underlying tissue, organs, etc. Several embodiments of the cannula with the tissue gripping elements are disclosed.

BRIEF DESCRIPTION OF THE DRAWINGS

Various embodiments are described with reference to the drawings, wherein;

FIG. 1 is a side view of a trocar assembly incorporating a cannula having external fixation structure provided thereon constructed in accordance with the present disclosure;

FIG. 1A is an isolated view of a fixation member of the cannula of FIG. 1;

FIG. 2 is a partial side view illustrating a second embodiment of an external fixation structure incorporated within a cannula;

FIG. 3 is a partial side view illustrating a third embodiment of the external fixation structure;

FIG. 4 is a partial side view illustrating a further embodiment of the external fixation structure;

FIG. 8 is a side view of a further embodiment of the external fixation structure in the form of a helical thread;

FIG. 9 is a side view of a further alternative embodiment of a cannula which is similar to the embodiment of FIG. 2;

FIG. 10 is a partial cross-sectional view of the fixation member of the embodiment of FIG. 9;

FIG. 11 is a longitudinal cross-sectional view of a portion of a cannula sleeve having a further alternative external fixation structure design;

FIG. 12 is a longitudinal cross-sectional view of a further cannula embodiment shown during insertion of the cannula through a patient's body wall; and FIG. 13 is a view similar to FIG. 12, which shows an external fixation structure deployed to a retaining position.

DETAILED DESCRIPTION OF THE PREFERRED EMBODIMENTS

Figure 5:
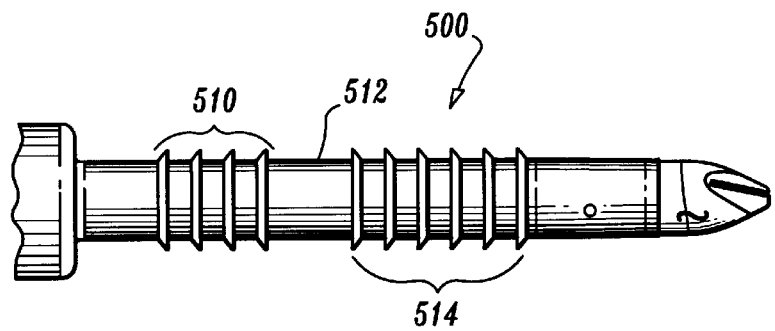
FIG. 5 is a partial side view of a further embodiment of a cannula having external fixation structure provided thereon which is similar to that provided on the embodiment of FIG. 1.

The present invention is particularly suited for use with surgical access devices including cannulas, catheters, endoscopic tubes, sheaths or the like. Such access devices are typically utilized in conjunction with a surgical procedure for introducing/withdrawing fluids or to permit insertion of additional instrumentation required to satisfactorily perform the surgical procedure. The following description of the present invention will be focused on its use with a surgical trocar or cannula assembly; however, it is appreciated that the present invention has application in any of the surgical access devices of the type listed hereinabove.

In the following description, as is traditional, the term "proximal" refers to the portion of the instrument closest to the operator while the term "distal" refers to the portion of the instrument remote from the operator.

Referring to the drawing figures wherein like reference numerals represent similar or identical elements and initially to FIG. I, there is illustrated a surgical trocar assembly 10 which incorporates the principles of the present invention. One suitable trocar assembly is disclosed in commonly assigned U.S. Pat. No. 4,601,710 to Moll, the contents of which are incorporated herein by reference. The presently disclosed cannula embodiments may be utilized in virtually any trocar assembly of the type having an outer sheath or cannula into which an obturator is inserted to provide access to a surgical site, particularly, in minimally invasive surgical procedures such as those performed, for example, endoscopically or laparoscopically. Briefly, the presently disclosed cannula embodiments provide numerous alternative designs for providing integral tissue gripping structure. Such structure is particularly advantageous in that it increases the retaining characteristics of a cannula within a body wall and also minimizes the potential of over insertion of the cannula. The structure also eliminates the need for additional separate anchoring mechanisms.

With reference to FIGS. 1 and 1A, trocar assembly 10 includes cannula 100 and obturator 1000 which is positionable in the cannula 100. Obturator 1000 includes an obturator housing 1002 and an obturator portion 1004 having pointed obturator tip or blade 1006 for penetrating tissue. In use, subsequent to insertion of trocar assembly in the tissue site, obturator 1000 is removed from cannula 100 leaving the cannula 100 in the tissue to serve as a portal for introduction of instrumentation.

Cannula 100 includes a cannula housing 102 and a cannula sleeve 104 connected to the housing 102 and extending distally therefrom. Cannula sleeve 104 defines longitudinal axis "a" and has an outer wall 106 which defines an inner longitudinal opening therein. Cannula 100 includes a first proximal series 110 of external fixation members such as rings 112 which taper outwardly away from the surface of cannula 100 in a generally distal direction. In this manner, a generally proximal oriented surface 112a is formed at an oblique angle relative to a longitudinal axis of cannula 100 and a distal facing planar surface 112b is formed transverse to a longitudinal axis of cannula 100. A second distal series 114 of external fixation members such as rings 116 are disposed distal of ring series 110. Rings 116 taper inwardly towards the surface of cannula 100 in a generally distal direction and form proximally facing planar surface 116a which is preferably transverse to the longitudinal axis "a" and distally oriented angled surface 116b as best depicted in FIG. 1A.

The above-noted structural arrangement provides for retention of cannula 100 in the body tissue due to the oppositely facing rings 112 and 116. Additionally, upon insertion, angled surfaces 116b of distal ring series 114 helps maintain relative ease of insertion of cannula 100. Preferably, angled surfaces 116b define an angle "x" ranging from about 10° to about 60° relative to the longitudinal axis "a" of cannula sleeve and, more preferably, about 45° relative to the longitudinal axis "a". Such arrangement of angled surface 116b minimizes the insertion force needed to advance cannula 100 in an insertion direction, indicated as arrow I, within the tissue "t".

Cannula 100 is continually advanced to a position whereby proximal ring series 110 reaches the tissue. At this juncture, planar surfaces 112b of series 112 engage the tissue. Planar transverse surfaces 112b effectively substantially increase the insertion force required to further insert cannula 100 thereby minimizing the potential of "over insertion" of the cannula 100. Moreover, rings 112 provide a tactile indication to the user that the cannula 100 has been sufficiently inserted to access the abdominal cavity and any further inserting movement may increase the potential of contact of the cannula with underlying tissue, organs, etc. When cannula 100 is situated with respect to the tissue, the opposing planar surfaces 112b of ring series 110 and 116a of ring series 114 serve as ledges to maintain cannula 100 at a fixed position within the tissue site, i.e., planar surfaces 112b resist movement of the cannula 100 in the insertion direction "I" while planar surfaces 116a resist movement of the cannula in the withdrawal direction "W".

Referring to FIG. 2, a proximal portion of cannula 200 features a series 210 of chevron or V-shaped raised surfaces 212, the apexes 214 of which point proximally. A distal portion of cannula 200 features a series 216 of chevron shaped raised surfaces 218, the apexes 220 of which point toward the distal end of cannula 200. With this arrangement, the insertion force is further reduced due to the streamline profile presented by the distal series 216. In all other respects, cannula 200 is similar to the cannula 100 of FIG. 1.

Referring to FIG. 3, a proximal half of cannula 300 features a series 310 of disjoined chevron shaped raised surfaces formed of disjoined segments 312a and 312b. A distal portion of cannula 300 features a series 314 of disjoined chevron shaped raised surfaces formed of segments 316a and 316b. This arrangement further reduces the insertion force required to insert the cannula by providing a longitudinal slot 320 as defined by the open apexes of series 310, 314 to which tissue displaced by the cannula during insertion may be received and pass.

Referring to FIG. 4, cannula 400 is the same as cannula 300 except that the proximal and distal raised surfaces 402,404 do not extend beyond the outer diameter of cannula 400, as shown by proximal and distal outer wall portions 406, 408, respectively, i.e., the surfaces are confined within the outer boundary of the cannula sleeve.

Referring to FIG. 5, cannula 500 is very similar to cannula 100 of FIG. 1 with two main exceptions. The first is that proximal and distal series 510, 514 are respectively displaced a predetermined distance. This provides a central tissue retaining region 512 between the two series 510, 514 which receives the proximal and distal surfaces of the tissue, such as, for example, the abdominal tissue, i.e., inclusive of the tissue between the epidermis and the peritoneal cavity lining.

Figures 6, 7:
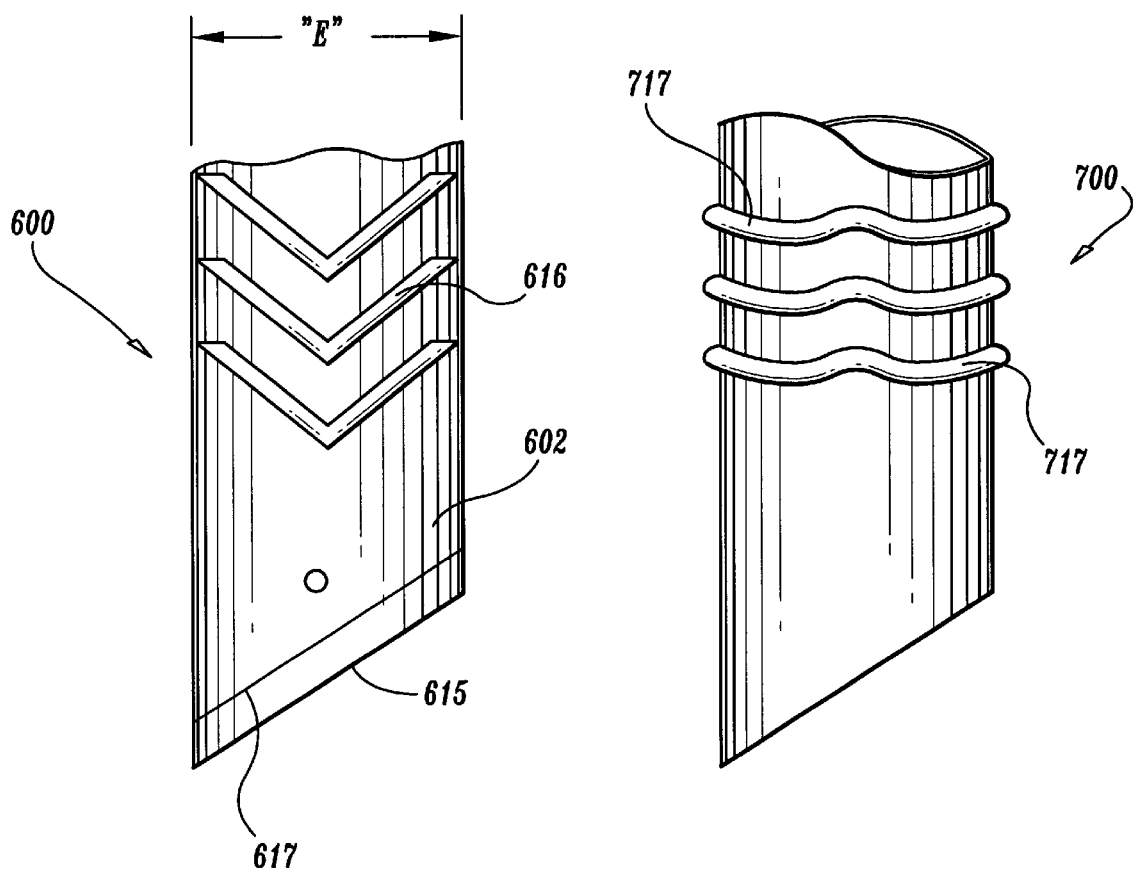
FIG. 6 is a partial side view of the distal end portion of a cannula illustrating another embodiment of a fixation structure pattern.
FIG. 7 is a partial side view of the distal end portion of a cannula having a further external fixation structure pattern formed thereon.

Referring to FIG. 6, cannula 600 is similar to cannula 200 except that raised chevron shaped portions 616 are formed within the boundaries of the outer diameter of cannula 600, i.e., the distance "e" across the chevron portions 116 is substantially equal to or less than the outer diameter of the cannula sleeve 602. Additionally, cannula 600 is provided with a beveled distal end 615 which has a chamfer 617 provided thereon. Chamfer 617 facilitates the initial insertion of cannula within the tissue site.

Referring to FIGS. 7–11, various alternative embodiments of cannulas are shown having different external fixation structure. With reference to FIG. 7, cannula 700 is provided with a series of sinusoidal shaped raised portions 717. Cannula 800 is provided with helical threads 816 thereon, as shown in FIG. 8. Cannula 900 is similar to cannula 200 of FIG. 2, except cannula 900 illustrates that different numbers of raised portion elements 912, 916 may be provided in the proximal and distal series 910, 914, respectively. FIG. 10 illustrates the cross-sectional shape of distally oriented chevron shaped raised portions 916 of FIG. 9. Raised portions 916 have angled surfaces 916 a and 916b. Surface 916a is angled such that it forms a greater angle of attack with the tissue proximal thereto and surface 916b provides a lesser angle of attack than surface 916a, with the distal tissue. In this embodiment, the proximal surface 916b is not transverse to the axis, but, may range from about 60°–90°. For proximal raised surface 912, the opposite relationship to that described in connection with raised surface 916 would apply.

Referring to FIG. 11, cannula 1000 is provided with a greater number of series 1002, 1004, 1006, 1008, and 1010 of raised portions wherein adjacent series have raised portions oriented in the opposite direction. Additionally, the proximal and distal surfaces of each raised portion is curved or arcuate.

Referring to FIGS. 12 and 13, cannula 1100 is provided with a tissue retention sleeve member 1110 coaxially mounted about the cannula sleeve 1105. Retention sleeve member 1110 may be fabricated from an elastomeric material and preferably formed, e.g., by injection molding techniques to define varying ridges 1112, 1114 when retention member is in an at rest condition, as shown in FIG. 13. Preferably, retention member 1110 is secured at a distal end to cannula 1100 by conventional means and is provided with finger levers 1116, 1118 at a proximal end. Finger levers 1116, 1118 may be formed of a rigid polymeric material or a suitable metal and secured to the proximal end of sleeve member by conventional means, or may be integrally formed with the sleeve member. In use, finger levers 1116, 1118 are retracted upon insertion of cannula 1100 through the body wall of the patient, as shown in FIG. 12. This stretches retention member 1110 thereby smoothing out ridges 1112, 1114. Once the cannula is situated in the desired position through the body wall, levers 1116, 1118 are released permitting ridges 1112, 1114 to assume their initial unactuated position thereby acting to resist proximal or distal movement of cannula 1100 with respect to the body wall. Alternatively, instead of being molded from an elastomeric material, retention member 1110 may be formed from one or more shape memory materials to achieve the above-noted results.

While the invention has been particularly shown and described with reference to certain preferred embodiments, it will be understood by those skilled in the art that various modifications in form and detail may be made therein without departing from the scope and spirit of the invention. Accordingly, modification to the preferred embodiments will be readily apparent to those skilled in the art, and the generic principles defined herein may be applied to other embodiments without departing from the spirit and scope of the invention. Thus, the present invention is not intended to be limited to the embodiments shown, but it is to be accorded the widest scope consistent with the principles and features disclosed herein.

What is claimed is:

1. A surgical access device for permitting introduction of instrumentation within tissue, which comprises:
    an elongate member defining a longitudinal axis and proximal and distal ends, the elongate member having an outer wall defining a longitudinal opening dimensioned for reception of surgical instrumentation;
    a first peripheral projection disposed on the outer wall of the elongate member, the first projection defining a proximal ledge dimensioned to resist movement of the elongate member in a first longitudinal direction corresponding to a withdrawal direction of the elongate member with respect to the tissue;
    a second peripheral projection disposed on the outer wall of the elongate member proximal of the first peripheral projection, the second projection defining a distal ledge dimensioned to resist movement of the elongate member in a second longitudinal direction corresponding to an insertion direction of the elongate member with respect to the tissue;
    the first and second peripheral projections each defining a substantially V-shaped configuration having a pair of segments extending to an apex region, the apex region of the first projection being disposed at a distalmost position of the first projection, the apex region of the second projection being disposed at a proximalmost position of the second projection; and
    the first and second peripheral projections cooperating to retain the elongate member within the tissue.

2. The surgical access device according to claim 1 including a plurality of first and second peripheral projections.

3. The surgical access device according to claim 2 wherein the pair of segments of the first and second projections are disjoined.

4. The surgical access device according to claim 1 including a first series of at least two first projections and a second series of at least two second projections disposed proximal of the first projection.

5. The surgical access device according to claim 4 including a plurality of first and second series arranged in alternating relationship along the longitudinal axis.

6. A surgical access device for permitting introduction of instrumentation within a surgical site, which comprises:
    an elongate member defining a longitudinal axis and having proximal and distal ends, the elongate member having an outer wall defining a longitudinal opening dimensioned for reception of surgical instrumentation;
    a first series of at least two first peripheral projections disposed on the outer wall of the elongate member, each first peripheral projection having a distal surface and a proximal surface, the distal surface arranged at an oblique angle with respect to the longitudinal axis and being dimensioned to permit movement of the elongate member in a first direction corresponding to an insertion direction of the elongate member with respect to the tissue, the proximal surface arranged to define a ledge dimensioned to engage tissue upon movement of the elongate member in a second longitudinal direction corresponding to a removal direction of the elongate member with respect to the tissue to facilitate retention of the elongate member therein; and
    a second series of at least two second peripheral projections disposed on the outer wall of the elongate member proximal of the first series, each second peripheral projection having a distal surface and a proximal surface, the distal surface arranged to define a ledge dimensioned to engage the tissue upon movement of the elongate member a predetermined distance in the first longitudinal direction to minimize over insertion of the elongate member with respect to the tissue.

7. The surgical access device according to claim 6 wherein the proximal surface of each second peripheral projection is arranged at an oblique angle with respect to the longitudinal axis and dimensioned to facilitate movement of the elongate member in the second direction corresponding to the removal direction of the elongate member upon insertion of the elongate member with respect to the tissue.

8. The surgical access device according to claim 7 wherein the first and second peripheral projections are substantially annular.

9. The surgical access device according to claim 6 wherein the first and second peripheral projections are generally V-shaped.

10. A surgical access device for permitting introduction of instrumentation within a surgical site, which comprises:

a substantially elongate member including an outer wall defining a longitudinal opening, with respect to a longitudinal axis thereof, for receiving and guiding a surgical instrumentation to a remote tissue site, the outer wall having a first peripheral projection defining proximal and distal surfaces, the distal surface arranged at an oblique angle with respect to the longitudinal axis and being dimensioned to permit movement of the elongate member in a first direction corresponding to an insertion direction of the elongate member with respect to the tissue site, the proximal surface arranged to define a ledge dimensioned to engage tissue upon movement of the elongate member in a second longitudinal direction opposed to the first longitudinal direction corresponding to a removal direction of the elongate member with respect to the tissue to facilitate retention of the elongate member therein, the outer wall having a second peripheral projection proximal of the first peripheral projection, the second peripheral projection having a distal surface and a proximal surface, the distal surface arranged to define a ledge dimensioned to engage the tissue upon movement of the elongate member a predetermined distance in the first longitudinal direction to minimize over insertion of the elongate member with respect to the tissue.

11. The surgical access device according to claim 10 wherein the ledges of the first and second peripheral projections are substantially transverse to the longitudinal axis of the elongate member.

12. The surgical access device according to claim 11 wherein the first and second peripheral projections are substantially annular.

13. The surgical access device according to claim 10 wherein the outer wall of the elongate member defines an outer boundary and wherein the first and second projections are confined within the outer boundary.

* * * * *